(12) United States Patent
Lemke et al.

(10) Patent No.: US 6,334,472 B1
(45) Date of Patent: Jan. 1, 2002

(54) APPARATUS FOR STERILIZING, FILLING AND SEALING PACKAGING CONTAINERS

(75) Inventors: Kuno Lemke, Bietigheim-Bissingen; Helmut Weber, Weinstadt-Beutelsbach, both of (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/100,324

(22) Filed: Jun. 19, 1998

(30) Foreign Application Priority Data

Jun. 20, 1997 (DE) .......................................... 197 26 222

(51) Int. Cl.[7] ................................................. B65B 1/04
(52) U.S. Cl. ........................... 141/91; 141/90; 422/292; 422/300; 422/302; 422/304; 134/61; 134/70; 134/71
(58) Field of Search ..................... 141/85, 89, 91–93; 134/61, 70, 71; 53/111 R; 99/483; 422/292, 300, 302, 304; 34/62, 105

(56) References Cited

U.S. PATENT DOCUMENTS 3,889,009 A 6/1975 Lipoma
5,022,165 A 6/1991 Beswick
5,792,435 A * 8/1998 Mueller et al. ............. 422/292

FOREIGN PATENT DOCUMENTS

| EP | 0206096 | 6/1986 |
| EP | 0312022 | 10/1988 |
| EP | 0570946 A1 | 5/1992 |
| FR | 2358163 | 6/1977 |
| FR | 2547732 | 6/1983 |

* cited by examiner

Primary Examiner—David J. Walczak
Assistant Examiner—Timothy L. Maust
(74) Attorney, Agent, or Firm—Edwin E. Greigg; Ronald E. Greigg

(57) ABSTRACT

An apparatus for sterilizing, filling and sealing containers has a sterilization chamber, a cooling chamber, and a filling and sealing chamber, through which the containers are conveyed by means of an endless conveyor device. For presterilizing the chambers before the apparatus is put into operation, these chambers are acted upon by a gaseous sterilizing agent flowing through them, which is fed through an inlet or an outlet for the containers. In order that regions less affected by the flowing sterilizing agent as it flows, because they are in the lee, will also be disinfected well, the flow direction of the sterilizing agent is changed multiple times. A blower with a reversible flow direction is used for this purpose.

3 Claims, 2 Drawing Sheets

APPARATUS FOR STERILIZING, FILLING AND SEALING PACKAGING CONTAINERS

BACKGROUND OF THE INVENTION

The invention is based on an apparatus for sterilizing, filling and sealing containers. Before being put into operation each time, the individual chambers as well as the filling and sealing devices built into them in such apparatus are sterilized by having a sterilizing agent in gaseous or vapor form, such as a mixture of hydrogen peroxide and air, flow through them and act on them for a predetermined period of time. To that end, the device for feeding the sterilizing agent into and through the chambers is designed so as to have the sterilizing agent flow in one direction through the chambers in succession. It sometimes happens that in corners reached only poorly by the sterilizing agent, germs will serve and will get into containers and into the product to be placed in them.

OBJECT AND SUMMARY OF THE INVENTION

The apparatus according to the invention has the advantage over the prior art that by reversing the flow direction of the sterilizing agent in the sterilization chamber and in the filling and sealing chamber, places in the lee of one flow direction are reached in the opposite flow direction, thus substantially increasing the reliability of the sterilization. Another advantage is that with increased sterilization reliability, the length of time needed to presterilize the apparatus is shortened, thus reducing the consumption of a sterilizing agent.

The invention will be better understood and further objects and advantages thereof will become more apparent from the ensuing detailed description of a preferred embodiment taken in conjunction with the drawings.

DESCRIPTION OF THE PREFERRED EMBODIMENTS

Figure 1:
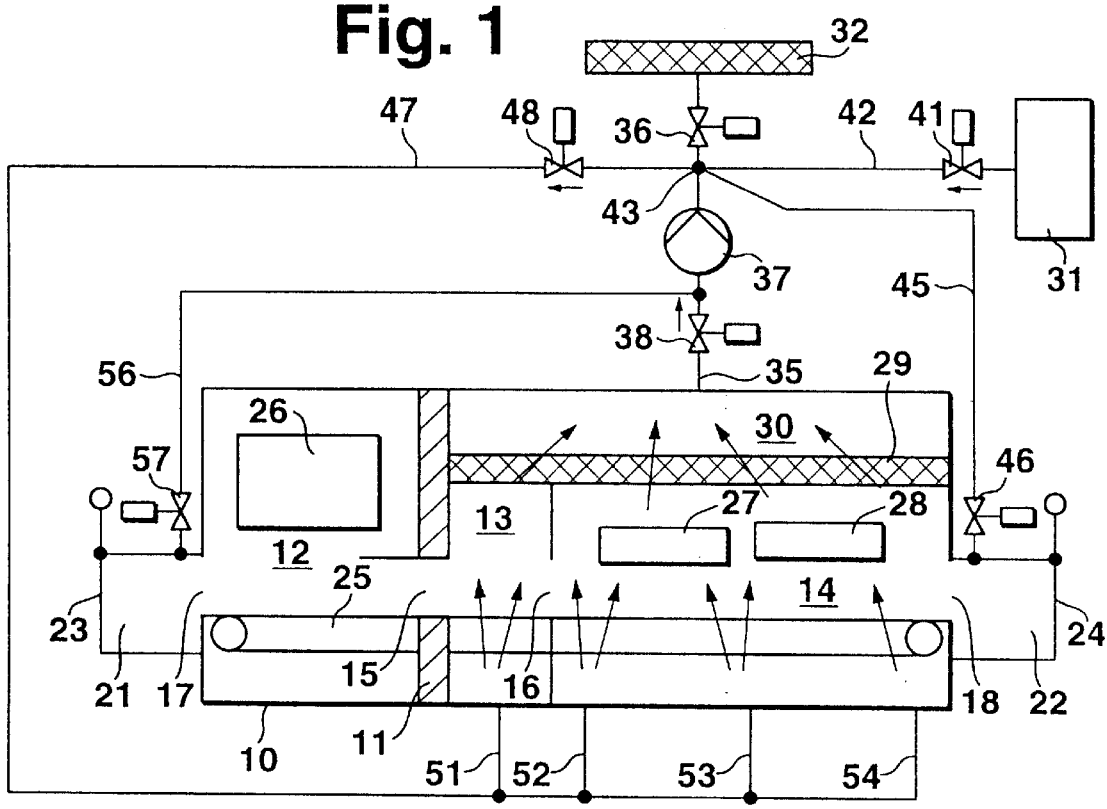
FIGS. 1–4 show an apparatus for sterilizing, filling and sealing containers in various indexing positions during presterilization and during operation.

In a boxlike housing 10, a sterilization chamber 12, a cooling chamber 13 and a filling and sealing chamber 14 are disposed side by side, separated by a heat-insulating partition 11 and communicating with one another through openings 15, 16. The sterilization chamber 12 has an inlet opening 17 and the filling and sealing chamber 14 has an outlet 18, each oriented coaxially with the openings 15, 16, and each preceded and following by a respective sluice 21, 22. The two sluices 21, 22 can be closed by means of flaps 23, 24. From the inlet opening 17 to the outlet opening 18, a linear conveyor device extends through the chambers 12, 13, 14, such as an endless conveyor chain 25, which carries the containers that are to be sterilized, filled and sealed, such as bottles, vials or similar heat-stressable packaging containers, through the chambers. A heating device 26 for heating the containers to the sterilization temperature is built into the sterilization chamber 12, and a filling device 27 and a sealing device 28 are built into the filling and sealing chamber 14. The top of the cooling chamber 13 and filling and sealing chamber 14 is formed by a superfine filter 29, which above itself defines an air distribution chamber 30.

To assure a high-quality sterility of the liquid products to be packed and packaged in the containers, such as vaccines, medicines, of foods, it is important that the containers be disinfected, filled and sealed in a completely sterile atmosphere in the apparatus. The apparatus is therefore equipped with a device that before the apparatus is put into operation presterilizes the chambers 12, 13, 14, through which the containers are carried, and the filling and sealing devices with a gaseous sterilizing agent, such as a mixture of hydrogen peroxide and air, and during operation keeps them at a slight overpressure in a sterile air atmosphere.

To that end, the chambers 12, 13, 14 can be made to communicate with sterilizing agent generator 31 and a sterile air source 32. A line 35 leads from the sterile air source 32 via a valve 36, a blower 37 whose feeding direction is reversible, and a second valve 38 in the air distribution chamber 30. A second line 42, which begins at the sterilizing agent generator 31 and can be blocked off by a valve 41, leads to a distributor 43 in the line 35 between the blower 37 and the valve 36 near the sterile air source 32. A line 45 also leads from the distributor 43 via a valve 46 into the sluice 22 at the outlet opening 18, and a line 47 leads via a valve 48 to the bottom of the cooling chamber 13 and filling and sealing chamber 14, where this line branches off and discharges with multiple branches 51, 52, 53, 54 into these chambers 13, 14. A line 56 with a valve 57 also connects the sluice 21 at the inlet opening 17 to the line 35 between the blower 37 and the air distribution chamber 30.

The apparatus described above is prepared for operation as follows:

First, the lines and the superfine filter 29 in the cooling chamber 13 and the filling and sealing chamber 14 are disinfected with a mixture of hydrogen peroxide and air (FIG. 1). To that end, the valves 46, 57 are connected to the sluices 21, 22, which are closed with the flaps 23, 24, and the valve 36 is connected to the sterile air source 32, and the other valves 41, 48, 38 are opened. The blower 37 is turned on, so that the blower feeds from the air distribution chamber 30 to the branch 43. After the valve 41 is opened, gaseous sterilizing agent flows from the sterilizing agent generator 31 through the lines 42 and 47 and the branches 51–54 through the cooling chamber 13 and the filling and sealing chamber 14 from below, sweeps past the fixtures built into them, penetrates the pores in the superfine filter 29, and via the air distribution chamber 30 reaches the blower 37, which feeds it in circulatory fashion into the line 47 via the distributor 43. Additional sterilizing agent is also delivered from the sterilizing agent generator 31 at overpressure.

Figure 2:
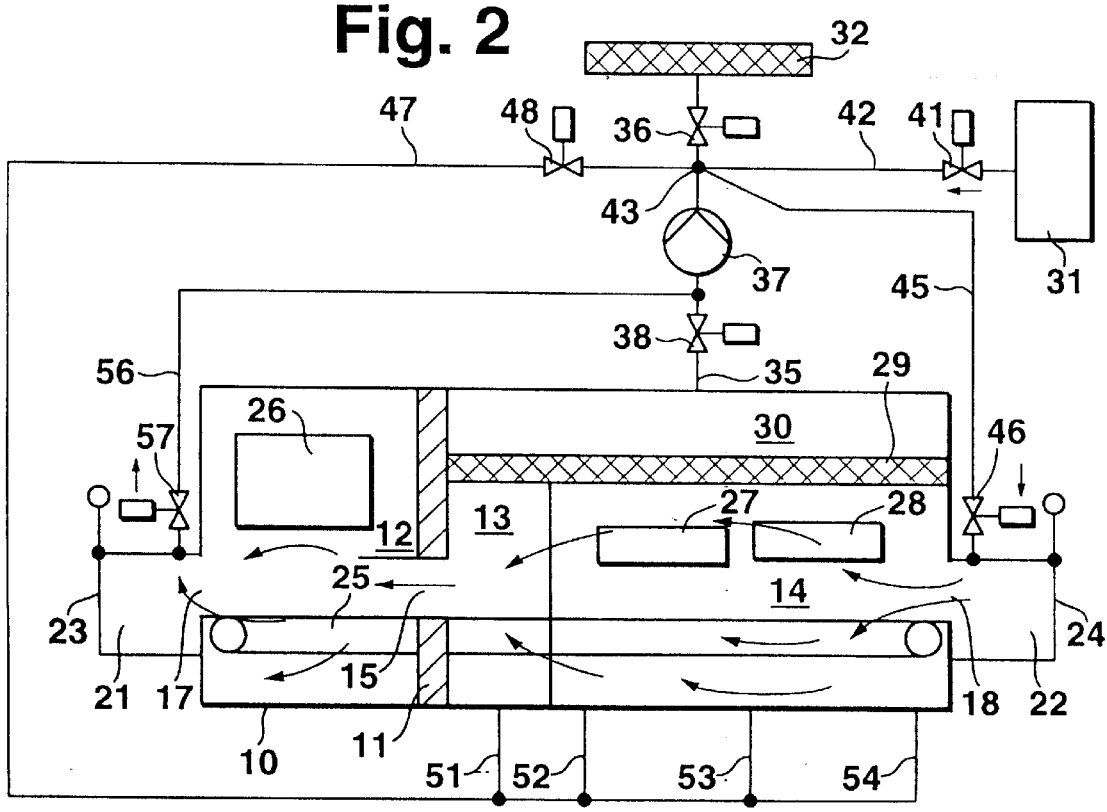
Figure 3:
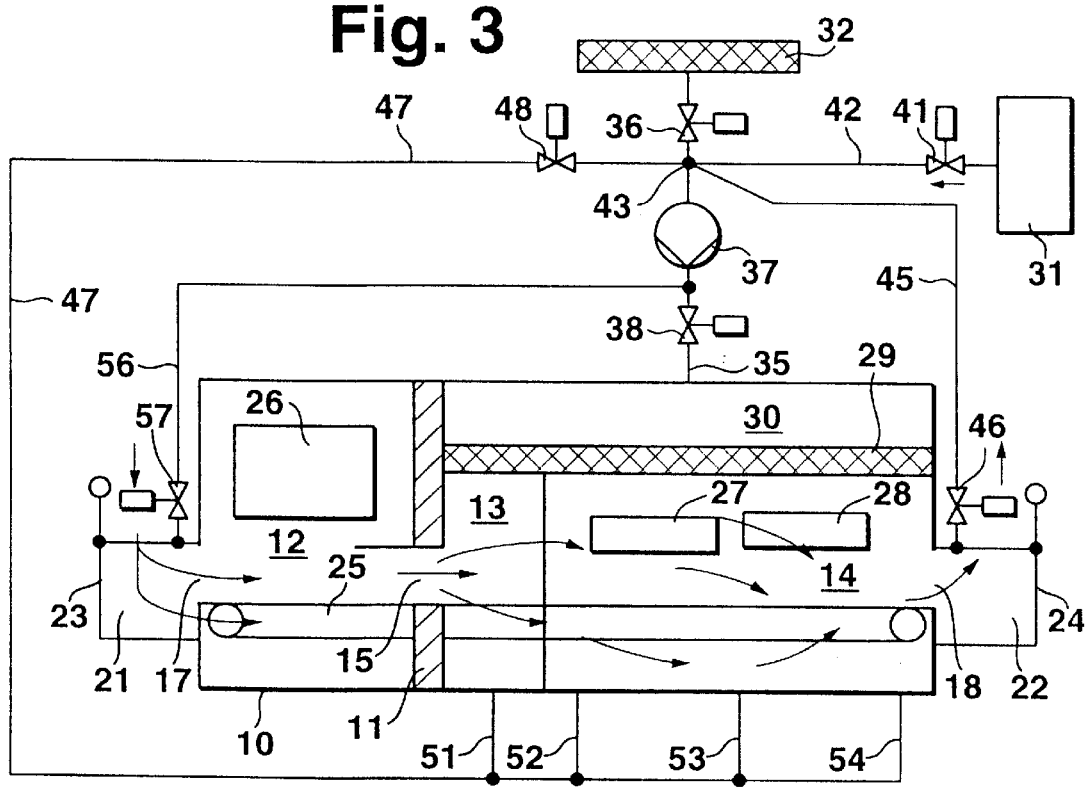

After an about five-minute treatment of the lines and the superfine filter 29, the valves 38 and 48 are now closed, and the valves 46 and 47 to the sluices 21, 22 are opened (FIG. 2), so that the sterilizing agent dispensed by the sterilizing agent generator 31 flows from the distributor 43 through the line 45 into the sluice, and from there through the outlet 18 into the filling and sealing chamber 14 and the cooling chamber 13. Through the opening, it reaches the sterilization chamber 12, and from there it flows through the inlet 17 into the sluice and through the line 56 to reach the blower 37. With the addition of more sterilizing agent delivered at overpressure, the circulating sterilizing agent is kept flowing in this direction of revolution for a few minutes. On flowing through the chambers 14, 13, 12, the sterilizing agent sweeps along its walls and the surfaces of the built-in fixtures, such as filling and sealing devices 27, 28.

Since in the flow around potruding parts, regions in the lee are acted upon by the sterilizing agent to a lesser extent, the direction of the flow is reversed after a certain duration of treatment. To that end, the blower 37 is reversed, so that it now feeds the sterilizing agent through the line 56 into the sluice 21 and through the inlet opening 17 first into the sterilizing agent 12 and from there through the opening 15 into the cooling chamber 13 and the filling and sealing chamber 14, through the outlet opening 18 and back to the blower 37 again through the closed sluice 22 and the line 45. The blower 37 keeps up this circulation of the sterilizing agent for a certain length of time, and an additional sterilizing agent is added continuously by the sterilizing agent generator 31.

The direction of the flow through the chambers 12, 13, 14 that are to be sterilized is perferably changed multiple times, so that finally even regions of the chambers 12, 13, 14 and their built-in fixtures that remain in the lee are disinfected to a high degree.

Figure 4:
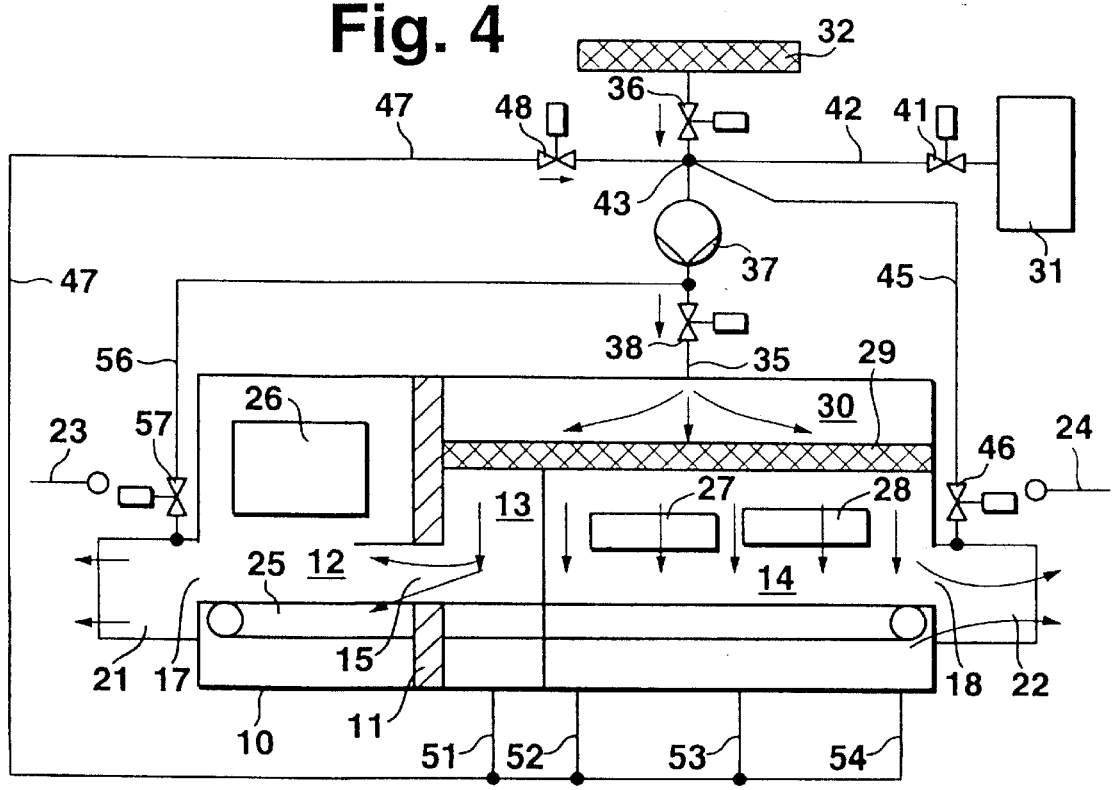

After presterilization lasting about 20 minutes, the chambers 12, 13 and 14 and their devices are flushed with sterile air (FIG. 4). Once the supply of sterilizing agent has been stopped, which is done by closing the valve 41, the valves are connected to the sluices 21, 22, and the valves 36 and 38 in the line 35 and the valve 48 in the line 47 are all opened. By switching the blower 37 to the feeding direction in which feeding is from the sterile air source 32 in the air distribution chamber 30, air flows through the sterile air source 32 through the valves 36, 38 into the air distribution chamber 30 and from there through the superfine filter 29, which is preferably an LF filter (laminar flow filter), in a laminar flow into and through the cooling chamber 13 and the filling and sealing chamber 14. The superfine filter 20 traps germs and dust particles, so that in the chambers 13 and 14, a sterile atmosphere at a slight ovepressure is built up and maintained. Air drawn off at the bottom through the branches 51, 52, 53, 54 and aspirated through the line 47 by the blower 37 via the distributor 43 is recirculated.

To begin the filling operation, after flushing has been done for a certain length of time, the flaps 23, 24 of the sluices 21, 22 are opened (FIG. 4). The containers to be filled are places on the conveyor chain 25 and are then first carried through the sterilization chamber 12. There, they are heated to a high sterilization temperature, at which germ adhering to them die off. After cooling down in the cooling chamber 13, the containers are then filled and sealed in the filling and sealing chamber 14, and they then pass out of the apparatus through the sluices 22. The air emerging through the opened sluices 21, 22 is replaced by aspirating fresh air through the sterile air source 32.

The foregoing relates to a preferred exemplary embodiment of the invention, it being understood that other variants and embodiments thereof are possible within the spirit and scope of the invention, the latter being defined by the appended claims.

We claim:

1. An apparatus for sterilizing, filling and sealing containers, comprising a sterilization chamber (12) with a closable inlet (17); a cooling chamber (13); a filling and sealing chamber (14) with a closable outlet (18); openings (15, 16) for connecting the sterilization chamber (12), cooling chamber (13) and filling and sealing chamber (14); and feed device (25) for conveying the containers through the sterilization chamber (12), cooling delivering a gaseous sterilizing agent and/or sterile air into the sterilization chamber (12), cooling chamber (13) and filling and sealing chamber (14) from a sterilizing agent generator (31) and/or a sterile air filter (32) through lines (35, 42, 45, 47, 56) that communicate with the sterilization chamber (12), cooling chamber (13) and filling and sealing chamber (14) said through lines include valves (36, 38, 41, 46, 48, 57) which can block-off said through lines; a blower (37) that feeds a sterilizing agent and/or a sterile air via said lines and said valves, the blower (37) is incorporated into a line connection (45, 56) between the inlet (17) of the sterilization chamber (12) and the outlet (18) of the filling and sealing chamber (14), and the feeding direction of the blower (37) is reversible.

2. An apparatus in accordance with claim 1, in which the line connection (45, 56) between the inlet (17) of the sterilization chamber (12) and the outlet (18) of the filling and sealing chamber (14) can be short-circuited by means of valves (46, 57).

3. An apparatus in accordance with claim 2, in which the inlet (17) of the sterilization chamber (12) and the outlet (18) of the filling and sealing chamber (14) each have a respective sluice (21, 22), to which the short-circuitable line connection (45, 46) is connected.

* * * * *